US010231886B2

(12) United States Patent
Schoenbeck

(10) Patent No.: US 10,231,886 B2
(45) Date of Patent: Mar. 19, 2019

(54) ELASTIC STRAP PART FOR DIAPER CLOSURE

(71) Applicant: MONDI Consumer Packaging Technologies GmbH, Gronau (DE)

(72) Inventor: Marcus Schoenbeck, Versmold (DE)

(73) Assignee: MONDI CONSUMER PACKAGING TECHNOLOGIES GMBH, Gronau (DE)

(*) Notice: Subject to any disclaimer, the term of this patent is extended or adjusted under 35 U.S.C. 154(b) by 441 days.

(21) Appl. No.: 15/146,574

(22) Filed: May 4, 2016

(65) Prior Publication Data

US 2016/0324697 A1 Nov. 10, 2016

(30) Foreign Application Priority Data

May 7, 2015 (EP) .................................. 15166806

(51) Int. Cl.
*A61F 13/494* (2006.01)
*A61F 13/49* (2006.01)
(Continued)

(52) U.S. Cl.
CPC .... *A61F 13/4902* (2013.01); *A61F 13/49015* (2013.01); *A61F 13/58* (2013.01); *B32B 3/10* (2013.01); *B32B 5/022* (2013.01); *B32B 5/08* (2013.01); *B32B 7/045* (2013.01); *B32B 7/12* (2013.01); *B32B 7/14* (2013.01); *B32B 27/08* (2013.01); *B32B 27/12* (2013.01);
(Continued)

(58) Field of Classification Search
CPC .......... A61F 13/49014; A61F 13/49015; A61F 13/4902; A61F 2013/49036; A61F 2013/49041; A61F 2013/586; A61F 2013/587
See application file for complete search history.

(56) References Cited

U.S. PATENT DOCUMENTS 7,150,732 B2 * 12/2006 Yoshida ............ A61F 13/49011
604/389
7,534,481 B2 5/2009 Seth
(Continued)

FOREIGN PATENT DOCUMENTS

EP 2106776 A 10/2009
EP 2158880 A 3/2010
(Continued)

*Primary Examiner* — Catharine L Anderson
(74) *Attorney, Agent, or Firm* — Andrew Wilford

(57) ABSTRACT

An elastic diaper part has an inelastic substrate layer having a wide inner end for connection to a diaper and a narrow and opposite outer end spaced in a stretch direction from the inner end, narrower than the inner end, and adapted for connection to a closure. An elastic film is juxtaposed and generally contiguous with the substrate layer, and there is an array of parallel adhesive strips extending transversely of the direction between the substrate layer and the elastic film. Each strip adheres the film to the substrate layer, and the strips are each of a respective strip width and separated by spaces each of a respective spacing width. The strip and/or spacing width varies from the inner end to the outer end such that the diaper part stretches uniformly between its inner and outer ends when stretched in the direction.

6 Claims, 4 Drawing Sheets

(51) Int. Cl.
| | | |
|---|---|---|
| *B32B 7/14* | (2006.01) | |
| *B32B 27/12* | (2006.01) | |
| *A61F 13/58* | (2006.01) | |
| *B32B 5/02* | (2006.01) | |
| *B32B 5/08* | (2006.01) | |
| *B32B 7/04* | (2019.01) | |
| *B32B 7/12* | (2006.01) | |
| *B32B 27/08* | (2006.01) | |
| *B32B 27/30* | (2006.01) | |
| *B32B 27/32* | (2006.01) | |
| *B32B 27/34* | (2006.01) | |
| *B32B 27/40* | (2006.01) | |
| *B32B 3/10* | (2006.01) | |
| *B32B 37/12* | (2006.01) | |
| *B32B 38/00* | (2006.01) | |

(52) U.S. Cl.
CPC ............ *B32B 27/302* (2013.01); *B32B 27/32* (2013.01); *B32B 27/34* (2013.01); *B32B 27/40* (2013.01); *A61F 2013/49036* (2013.01); *A61F 2013/49041* (2013.01); *B32B 37/1292* (2013.01); *B32B 2038/0028* (2013.01); *B32B 2262/0253* (2013.01); *B32B 2262/0261* (2013.01); *B32B 2262/0276* (2013.01); *B32B 2262/062* (2013.01); *B32B 2262/12* (2013.01); *B32B 2262/14* (2013.01); *B32B 2274/00* (2013.01); *B32B 2307/51* (2013.01); *B32B 2307/54* (2013.01); *B32B 2307/72* (2013.01); *B32B 2307/732* (2013.01); *B32B 2555/02* (2013.01)

(56) References Cited

U.S. PATENT DOCUMENTS

| | | | |
|---|---|---|---|
| 8,287,511 B2* | 10/2012 | Mitsui | ............... A61F 13/49466 604/385.01 |
| 8,304,355 B2 | 11/2012 | Baldauf | |
| 8,716,547 B2 | 5/2014 | Venkitaraman | |
| 2011/0151739 A1 | 6/2011 | Bosler | |
| 2017/0157901 A1* | 6/2017 | Uchida | .................. A41D 13/00 |

FOREIGN PATENT DOCUMENTS

| | | |
|---|---|---|
| WO | 2006124337 A | 11/2006 |
| WO | 2008021701 A | 2/2008 |

* cited by examiner

ELASTIC STRAP PART FOR DIAPER CLOSURE

FIELD OF THE INVENTION

The present invention relates to a diaper closure. More particularly this invention concerns an elastic strap part for connecting the diaper closure to an edge of a diaper.

BACKGROUND OF THE INVENTION

The strap part that extends between at least one side of the diaper closure and the actual diaper is typically a laminate that has at least one substrate layer and an elastic film bonded to the substrate layer and is elastically stretchable in a stretch direction at least in the region of the elastic film. The laminate has an inner end for attachment to the diaper and an outer end for the closure. The outer end has a narrower width transverse to the stretch direction than the inner end. In an elastic region between the inner and outer ends, the substrate layer is joined to the elastic film by a plurality of parallel adhesive strips that extend transverse to the stretch direction. Such a diaper part is in practice frequently also referred to as a diaper ear (back ear laminate).

An elastic diaper part having these features is known for example from WO 2006/124337. The adhesive joining the elastic film to the substrate layer made for example of a nonwoven is formed by a plurality of parallel and spaced adhesive strips that extend transverse to the stretch direction. Compared to surface bonding, such an array improves the elastic stretching properties of the laminate. Typically, the elastic region of the diaper part is mechanically activated by stretching. The application in strips of the adhesive improves the activation capability and the effectiveness of the activation. Within the known measures, the adhesive strips of the array all have the same width and are set at the same uniform spacing. In fact in WO 2006/124337, the width of the adhesive strips and the spacing between the strips have a fixed ratio specified within a range between 0.33 and 1.0.

US 2011/0151739 (EP 2,158,888) describes a laminate from which diaper parts can be stamped in a multi-web stamping process. The laminate has an elastic substrate film and nonwoven cover layers that are adhered to each other. It also has regions surface-bonded to each other and strip-shaped adhered regions. The adhesive strips form a pattern that comprises adhesive strips of varying width and/or arranged with varied spacing. The array thus has no relationship to the shape of the diaper parts stamped out from the laminate.

The prior-art laminates are distinguished by satisfactory stretching properties if the stretching measurements are made on laminate strips of constant width. In a tensile test on test pieces, which are typically standardized with regard to their dimensions, stretching properties can be uniformly measured.

In the case of diaper parts that are manufactured as so-called diaper ears and have an inner wide attachment end for attachment to a diaper and a narrow outer end for a closure, it has been observed that the elongation is not uniform when the laminate is stretched in the stretch direction. At the narrow attachment end, the elastic region of the diaper part is subject to a greater tensile stress and stretches more than the elastic region of the laminate adjacent the wide attachment end. Near the wide attachment end, better stretching is required, while on the outer end a higher strength is desirable.

OBJECTS OF THE INVENTION

It is therefore an object of the present invention to provide an improved elastic strap part for a diaper closure.

Another object is the provision of such an improved elastic strap part for a diaper closure that overcomes the above-given disadvantages, in particular with a better distribution of the performance of the elastic diaper part between the inner and outer ends.

In particular, the object is that the stretching properties of a diaper part having an inner wide attachment end and an outer narrow attachment end are uniform across the elastic region, so that the elastic region of the diaper part adjacent inner end is stretched just as much as adjacent the outer end if the diaper part is stretched when used.

SUMMARY OF THE INVENTION

An elastic diaper part has according to the invention a substrate layer having a wide inner end of predetermined width adapted for connection to a diaper and a narrow and opposite outer end spaced in a stretch direction from the inner end, of narrower width than the inner end, and adapted for connection to a closure. A width transverse to the direction of the substrate layer decreases from the wide outer end to the narrow inner end. An elastic film is juxtaposed and generally contiguous with the substrate layer, and there is an array of parallel adhesive strips extending transversely of the direction between the substrate layer and the elastic film. Each strip adheres the film to the substrate layer, and the strips are each of a respective strip width and separated by spaces each of a respective spacing width. The strip and/or spacing width varies from the inner end to the outer end such that the diaper part stretches uniformly between its inner and outer ends when stretched in the direction.

The area covered by of the adhesive of the adhesive strips changes relative to the area of the spaces between the strips changes depending on the width of the laminate. The portion of area covered by of the adhesive strips increases as the laminate width becomes smaller.

According to the present invention, the width of the adhesive strips and/or the spacing between adjacent adhesive strips is predetermined, depending on the width of the laminate, in such a way that stretching of the elastic region is essentially uniform when the laminate is stretched in the stretch direction.

The adhesive strips can in particular have a width between 0.5 mm and 1.2 mm. The spacing between the adhesive strips can vary between 0.5 mm and 2.0 mm. According to a preferred embodiment of the invention, the adhesive strips have a constant width between 0.5 and 1.2 mm, while the spacing between the adhesive strips is not constant and has a value specified, depending on the width of the laminate, between 0.5 mm and 2.0 mm. Alternatively, the spacing between the adhesive strips can be constant and the width of the adhesive strips can be varied, depending on the respective laminate width.

Hot-melt adhesive is preferably used as the adhesive for the adhesive strips the elastic film to the substrate layer. For example, adhesives on the basis of styrene-olefin-styrene block copolymers are suitable.

The elastic region of the laminate is preferably mechanically activated. The mechanical activation of the laminate is accomplished via a so-called ring roll process in which the laminate runs through a pair of profile rollers and the laminate is locally overstretched in the gap between the profile rollers. The mechanical activation is visible on the finished product in the form of so-called activation strips. The activation strips are strip-shaped zones in which the material has been subjected to an overstretching alternating with zones in which there little or no overstretching has taken place. The activation strips extend transverse to the stretch direction and run parallel to the adhesive strips.

The substrate layer is preferably made of a nonwoven material. The nonwoven material is not subject to any limitations regarding the fiber material and the type of solidification. Polyolefins, in particular polyethylene and polypropylene, polyester, polyamide, cellulose and two-part fibers and combinations of these fibers, come into consideration as the fibers. The nonwoven material can have in particular an area density between 8 g/m² and 50 g/m².

The elastic film is made of a thermoplastic elastomer, wherein in particular polymers from the group of styrene-butadiene-styrene block copolymers (SBS), styrene-isoprene-styrene block copolymers (SIS), styrene-ethylene-butadiene-styrene block copolymers (SEBS), of elastic polyethylene copolymers, elastic polypropylene copolymers, elastic polyurethane copolymers, elastic polyamide copolymers and mixtures of these polymers are suitable. In addition to a use of monofilms, coextruded films can also be used, and coextruded films having multiple identical layers are likewise suitable. The elastic film can in particular have a thickness between 10 μm and 130 μm.

According to a preferred version of the invention, the elastic film is between two substrate layers made of nonwoven material and bonded to it, and the adhesive bonds on both sides of the elastic film are completed in the manner described above.

The attachment ends of the laminate for attachment to a diaper and for connection of a closure are appropriately designed to be relatively inelastic. The inner end for attachment to a diaper is appropriately designed to be soft and flexible. If the diaper part has an elastic film that is laminated between two nonwoven layers, the elastic film preferably terminates before the inner end, and the inner end is made up of just the two nonwoven layers that are bonded to each other. Preferably, the two nonwoven layers are surface-bonded to each other at the inner end. The outer end for attachment of a closure is preferably stiffened by a reinforcement layer that is bonded to the elastic film that is incorporated in the lamination in an overlap area.

The reinforcement layer is preferably made of a polymer that has a greater bending stiffness and greater tensile strength than the elastic film. The individual layers are preferably surface-bonded to each other in the area of the outer end. It is also within the scope of the invention that an inelastic strip having hook elements is provided at the outer end and is bonded to the elastic film of the laminate and/or a substrate layer made of nonwoven material, for example.

BRIEF DESCRIPTION OF THE DRAWING

The above and other objects, features, and advantages will become more readily apparent from the following description, reference being made to the accompanying drawing in which.

SPECIFIC DESCRIPTION OF THE INVENTION

As seen in FIGS. 1-4 an elastic diaper part in practice also referred to as a diaper ear is made of a laminate that has at least one substrate layer 1 and an elastic film 2 bonded to the substrate layer 1 and elastically stretchable in a stretch direction A at least in the region of the elastic film 2. According to a preferred embodiment of the invention, the elastic film 2 is laminated between two substrate layers 1 and is bonded thereto, each of the substrate layers 1 being made of a nonwoven web. The substrate layers 1 are not elastic but are stretchable to a limited degree.

Figure 2:
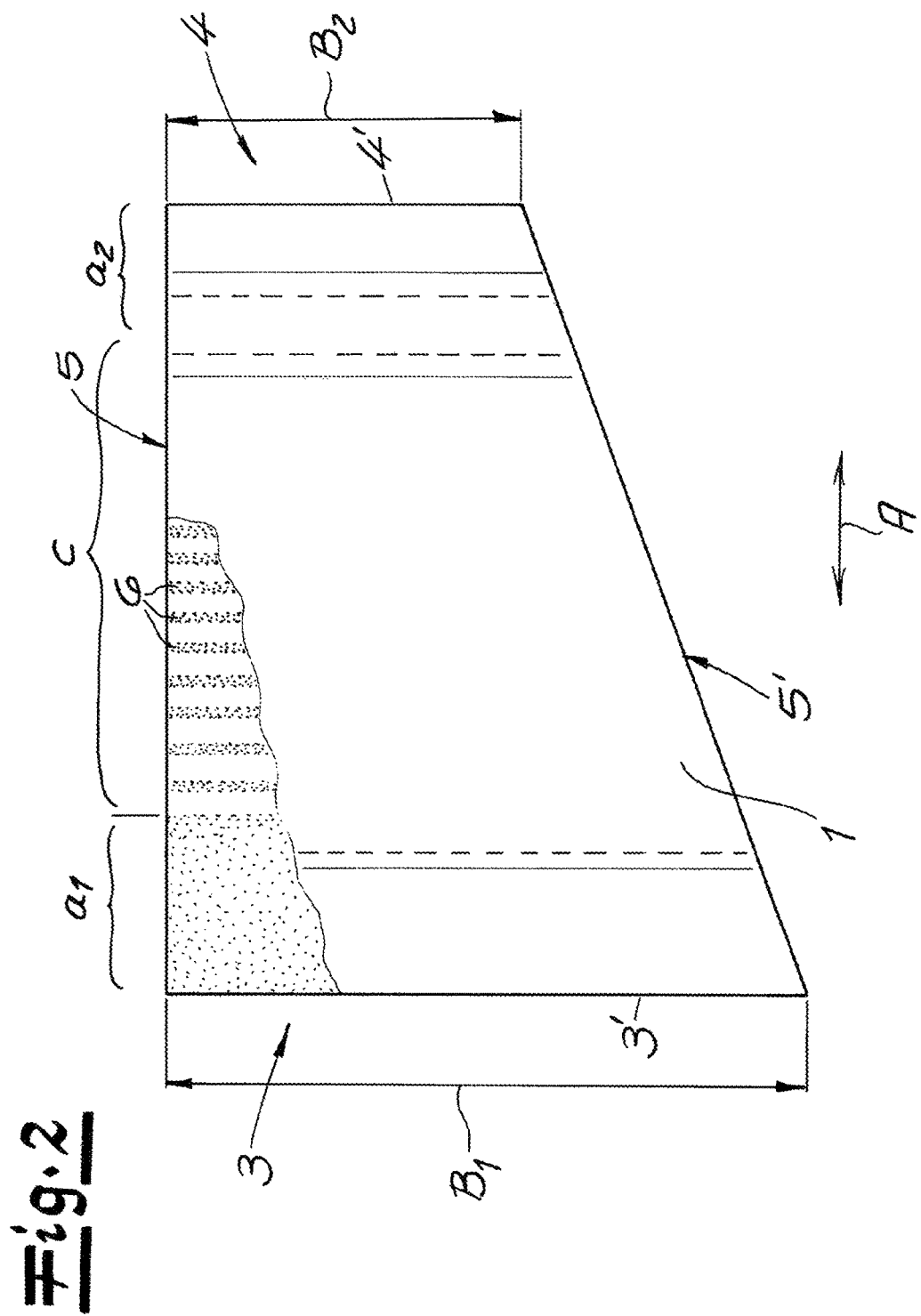
FIG. 2 is a top view of the diaper part shown in FIG. 1.

According to FIG. 2, the laminate has an inner end 3 for attachment to a diaper and an outer end 4 for a closure, for example a tape or a closure part provided with hooks of a hook/loop fastener. The ends 3 and 4 define inner and outer end edges 3' and 4'. The outer end 4 has a narrower width $B_2$ transverse to the stretch direction than the inner end 3 of width $B_1$. Here, the diaper part has the shape of a quadrilateral, the end edges 3' and 4' running parallel to each other and the two long sides 5 and 5' being oriented skewed relative to each other. The diaper part thus is a right trapezoid. Furthermore, the long sides 5 and 5' can also be curved in the shape of a bow.

The diaper part has inelastic zones $a_1$ and $a_2$ at the attachment ends 3 and 4. Between the inelastic zones $a_1$ and $a_2$, the diaper part has an elastic region c. In this elastic region c between the inner and outer ends 3 and 4, the elastic film 2 is bonded to the outer substrate layer 1 made of nonwoven material by a plurality of parallel adhesive strips 6. The adhesive strips 6 extend transverse to the stretch direction A.

Figure 1:
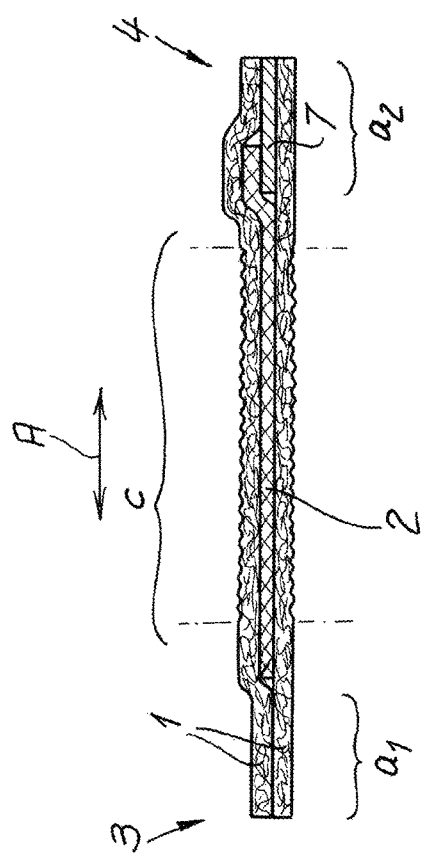
FIG. 1 is a longitudinal section through an elastic diaper part in the stretching direction.
Figure 4:
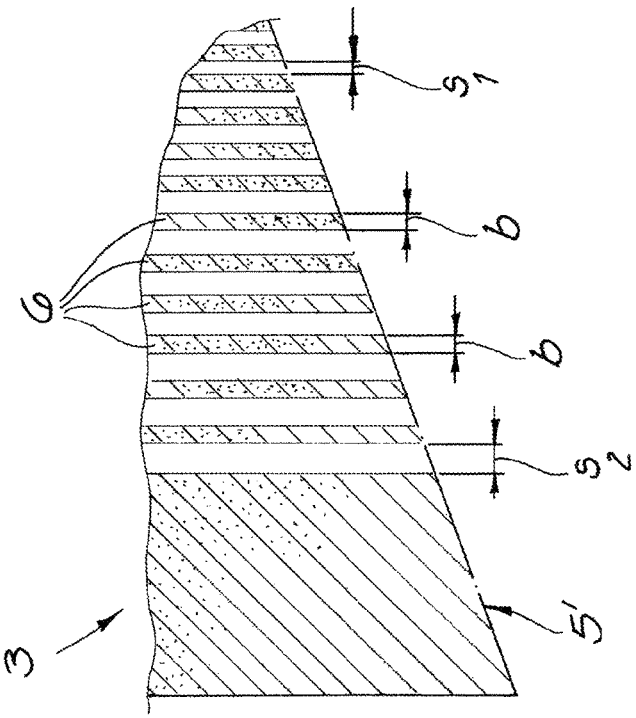
FIG. 4 is a large-scale view of a detail from FIG. 3.
Figure 3:
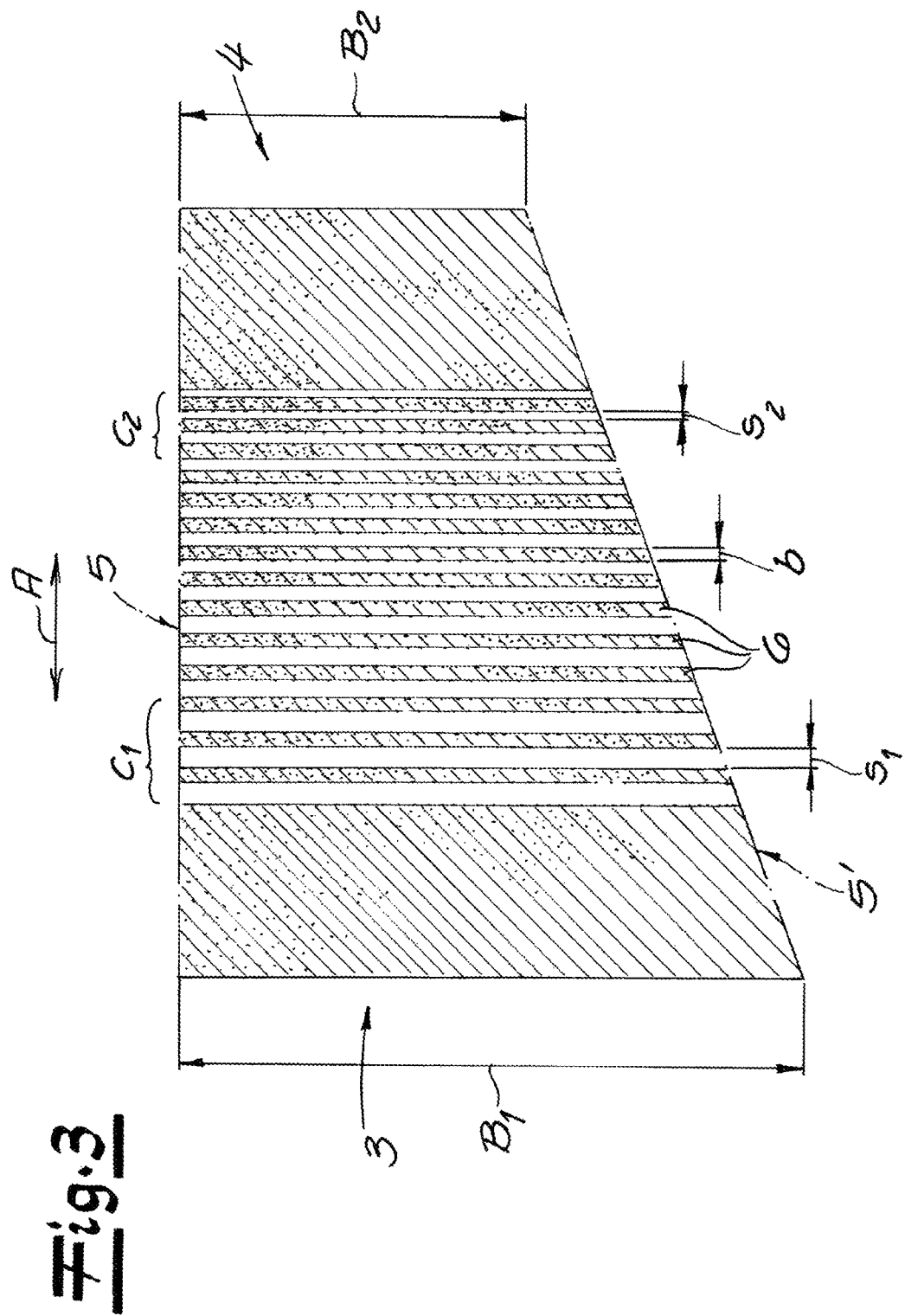
FIG. 3 shows the array of an adhesive bond between a substrate layer and an elastic film of the diaper part shown in FIGS. 1 and 2.

The array of the adhesive bonds between the elastic film 2 and the two outer substrate layers 1 is shown in FIGS. 3 and 4. The adhesive strips 6 form an array that has a smaller spacing $s_2$ between adjacent adhesive strips 6 in a region $c_2$ adjacent the outer end 4 than in a region $c_1$ adjacent the inner end 3. The regions $c_1$ and $c_2$ each comprise at least two adhesive strips 6 having an adhesive-free intermediate space between the adhesive strips. In the embodiment shown in FIGS. 3 and 4, the adhesive strips 6 have a constant width b of, for example, 1.0 mm, the width b being specified in a value range between 0.5 mm and 1.5 mm. The spacing s between the adhesive strips 6 changes as a function of the width B of the laminate and, depending on the width of the laminate, has values specified between 0.5 mm and 2.0 mm.

Figure 5:
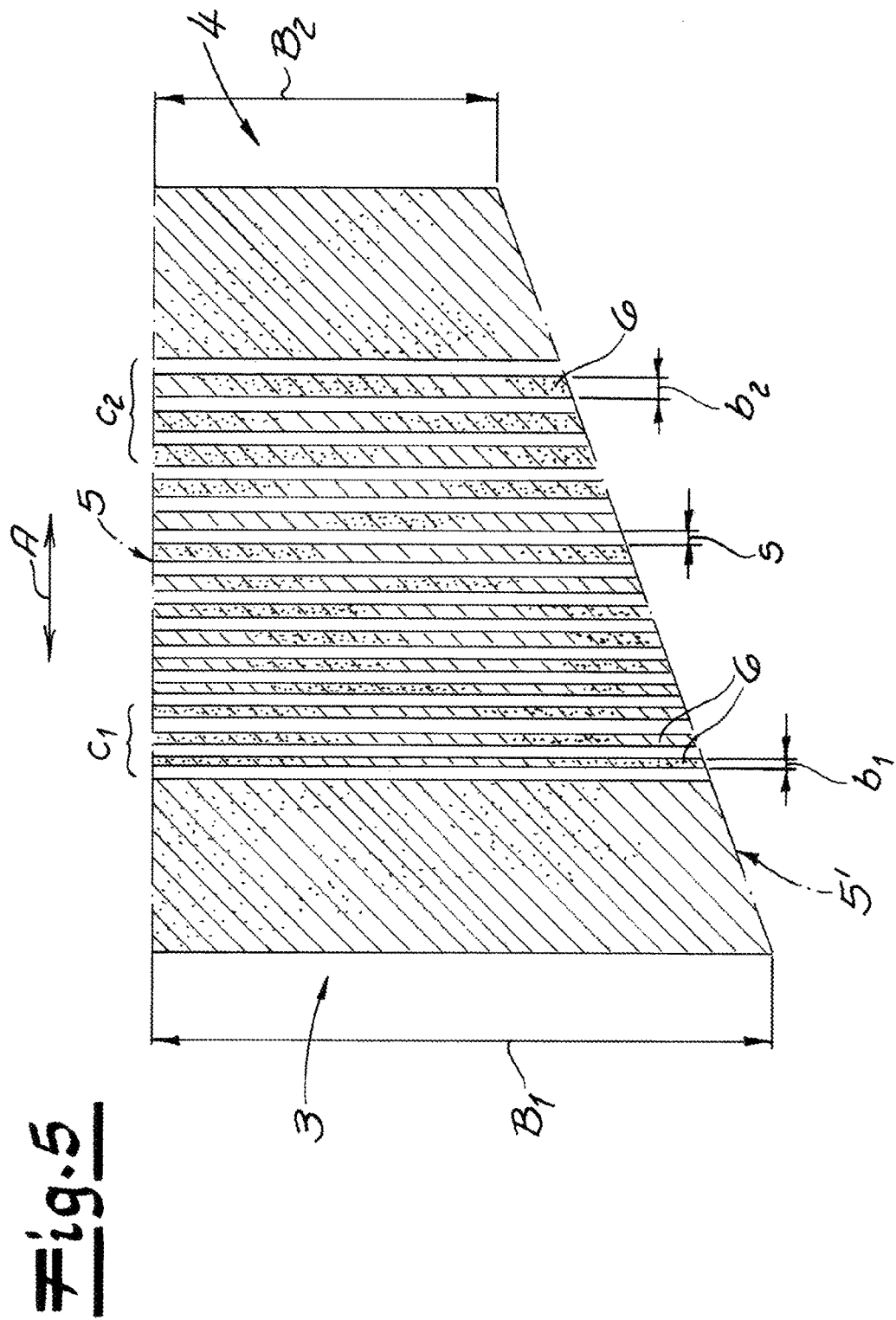
FIG. 5 is a view like FIG. 3 showing an alternative form of the invention.

According to an embodiment shown in FIG. 5, the spacing s between the adhesive strips 6 is constant and the width of the adhesive strips 6 varies from a wide width $b_2$ in a region $c_2$ adjacent the narrow end to a narrow width $b_1$ adjacent an inner region $c_1$ at the inner end 4. In a region $c_2$ adjacent the outer end 4, the adhesive strips 6 are wider than in the region $c_1$ adjacent the inner end 3.

The measures shown in FIGS. 3 to 5 can also be combined with one another. According to the invention, the portion of the adhesive area formed by the adhesive strips 6 and the base region, which comprises the adhesive region and the adhesive-free regions, changes depending on the width B of the laminate. Thus, the portion of the adhesive region relative to the base region increases as the width B of the laminate becomes smaller. Preferably, the width b of the adhesive strips 6 and/or the spacing s between adjacent adhesive strips 6 is set depending on the width B of the laminate in such a way that stretching of the elastic region c is essentially uniform when the laminate is stretched in the stretch direction. The distribution of adhesive according to the invention depends on the geometry of the diaper part, and results in uniformity of stretching of the diaper part so that when the diaper part is extended in the stretch direction, the elastic region $c_2$ near the outer end 4 extends just as much as the elastic region $c_1$ adjacent the inner end. This results in a better distribution of the performance of the diaper part.

The elastic region c of the laminate is mechanically activated. For mechanical activation, the laminate runs through a profile roller arrangement and is locally overstretched, that is stretched beyond its elastic limit, in the roller gap between the profile rollers. The mechanical activation is visible on the finished product in the form of so-called activation strips. The activation strips extend parallel to the adhesive strips 6 and bring about an improvement of the extensibility of the material. The attachment ends 3 and 4 of the laminate are designed as inelastic zones $a_1$ and $a_2$ whose layer structure is different at the inner and outer ends 3 and 4. The inner end 3, which has a large width $B_1$ and is attachable to a diaper, is soft and flexible and is made up of just the two substrate layers 1 made of nonwoven material that are bonded to each other. The elastic film 2 terminates before the inner end 3. In the inelastic zone $a_1$, the layers 1 and 2 are surface-bonded to each other. The surface-bonded adhesive bond extends past the edge of the elastic film 2 into a region of the elastic film 2 close to the edge. The outer end, to which a closure in the form of, for example, a hook or barb tape is attachable, is stiffened by a reinforcement layer 7 that is anchored in an overlap area on the section of the diaper part provided with the laminated-in elastic film 2. The overlap area can be about 2 mm to 10 mm wide. The reinforcement layer 7 is made of a polymer that, compared to the mechanical properties of the elastic film 2, is distinguished by a greater bending stiffness and high tensile strength.

I claim:

1. An elastic diaper part comprising:
   a substrate layer having an inner end of predetermined width adapted for connection to a diaper and an opposite outer end spaced in a direction of stretch from the inner end, of narrower width than the inner end, and adapted for connection to a closure, a width transverse to the direction of the substrate layer decreasing from the outer end to the inner end;
   an elastic film juxtaposed and generally contiguous with the substrate layer; and
   an array of parallel adhesive strips extending transversely of the direction, between the substrate layer and the elastic film, and each adhering the film to the substrate layer, the strips each being between the inner end and the outer end of a respective constant strip width of between 0.5 mm and 1.5 mm and separated by spaces each of a respective spacing width varying between the inner end and the outer end from 0.5 mm to 2.0 mm such that the diaper part stretches uniformly between its inner and outer ends when stretched in the direction and such that a portion covered by the adhesive strips increases toward the outer end.

2. The diaper part defined in claim 1, wherein the substrate layer is stretch-activated.

3. The diaper part defined in claim 2, wherein the substrate layer is a nonwoven.

4. The diaper part defined in claim 3, wherein there are two nonwoven substrate layers sandwiching the film and there are two arrays of adhesive strips each between a respective one of the substrate layers and a respective face of the film.

5. The diaper part defined in claim 4, wherein further comprising:
   means stiffening the substrate layer only immediately adjacent each of the ends.

6. The diaper part defined in claim 5, wherein the stiffening means is a stiff layer laminated between the substrate layers at least at the narrow outer end.

\* \* \* \* \*